US009006291B2

(12) United States Patent
Brinkenhoff

(10) Patent No.: US 9,006,291 B2
(45) Date of Patent: Apr. 14, 2015

(54) COMPOSITION, METHOD AND KIT FOR ENHANCING HAIR

(71) Applicant: Pharma Patent Holding Inc., Ventura, CA (US)

(72) Inventor: Michael C. Brinkenhoff, Ventura, CA (US)

(73) Assignee: Pharma Patent Holding Inc., Ventura, CA (US)

( * ) Notice: Subject to any disclaimer, the term of this patent is extended or adjusted under 35 U.S.C. 154(b) by 0 days.

(21) Appl. No.: 13/631,193

(22) Filed: Sep. 28, 2012

(65) Prior Publication Data

US 2013/0046024 A1  Feb. 21, 2013

Related U.S. Application Data

(63) Continuation of application No. 12/698,823, filed on Feb. 2, 2010, now abandoned.

(60) Provisional application No. 61/149,661, filed on Feb. 3, 2009.

(51) Int. Cl.
| A61K 8/42 | (2006.01) |
| A61K 31/165 | (2006.01) |
| C07C 405/00 | (2006.01) |
| A61Q 5/00 | (2006.01) |
| A61Q 7/00 | (2006.01) |
| A61K 8/69 | (2006.01) |

(52) U.S. Cl.
CPC ......... *A61K 31/165* (2013.01); *C07C 405/0041* (2013.01); *A61Q 5/00* (2013.01); *A61Q 7/00* (2013.01); *A61K 8/69* (2013.01); *C07C 2101/08* (2013.01)

(58) Field of Classification Search
CPC .. A61K 31/165; A61K 8/69; C07C 405/0041; C07C 2101/08; A61Q 5/00; A61Q 7/00
USPC .......... 514/622; 132/221; 428/34.1; 564/189
See application file for complete search history.

(56) References Cited

U.S. PATENT DOCUMENTS

| 3,382,247 A | 5/1968 | Anthony et al. |
| 3,644,363 A | 2/1972 | Kim |
| 3,922,297 A | 11/1975 | Pike |
| 3,931,282 A | 1/1976 | Muchowski et al. |
| 3,985,791 A | 10/1976 | Muchowski et al. |
| 4,005,133 A | 1/1977 | Morozowich |
| 4,116,989 A | 9/1978 | Nelson |
| 4,139,619 A | 2/1979 | Chidsey, III |
| 4,217,360 A | 8/1980 | Vorbrueggen et al. |
| 4,599,353 A | 7/1986 | Bito |
| 4,912,235 A | 3/1990 | Cooper et al. |
| 4,968,812 A | 11/1990 | Wang et al. |
| 5,001,153 A | 3/1991 | Ueno et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,352,708 A | 10/1994 | Woodward et al. |
| 5,387,608 A | 2/1995 | Andrews |
| 5,422,368 A | 6/1995 | Stjernschantz et al. |
| 5,422,369 A | 6/1995 | Stjernschantz et al. |
| 5,457,131 A | 10/1995 | Andrews |
| 5,510,383 A | 4/1996 | Bishop et al. |
| 5,516,796 A | 5/1996 | Stjernschantz et al. |

(Continued)

FOREIGN PATENT DOCUMENTS

| CA | 2401731 | 10/2001 |
| CA | 2735825 | 3/2010 |

(Continued)

OTHER PUBLICATIONS

Jean-Pierre Begue & Daniele Bonnet-Delpon, Recent Advances (1995-2005) in Fluorinated Pharmaceutical Based on Natural Products, 127 J Fluor. Chem. 992 (2006).*
Investigative Ophthalmology and Visual Science, 1984, ARVO Abstract, 266.
The Journal of Investigative Dermatology, Apr. 1996, vol. 106, No. 4, Abstracts, 858-957.
ARVO Abstracts (4) and (5), Experimental Eye Research, vol. 44, No. 6, Jun. 1987, 266.
Complaint for Patent Infringement, U.S. District Court, Middle Court of North Carolina, *Allergan, Inc.* et al., v. *Apotex Inc.* et al., Case No. 1:10-CV-681, Document 1, filed Sep. 8, 2010, 12 pages.
Answer, Defenses and Counterclaims of Defendants Apotex Inc. and Apotex Corporation, U.S. District Court, Middle Court of North Carolina, *Allergan, Inc.* et al., v. *Apotex Inc.* et al., Case 1:10-CV-681, Document 24, filed Nov. 22, 2010, 20 pages.

(Continued)

*Primary Examiner* — Sean Basquill
(74) *Attorney, Agent, or Firm* — Blakely Sokoloff Taylor & Zafman LLP

(57) ABSTRACT

Compositions for application and methods of application of a composition to modify hair. In one embodiment, a composition includes a compound (molecule) represented by:

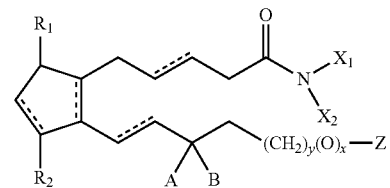

wherein A and B are individually selected from a hydrogen, a hydroxyl group and a halogen, with the proviso that when one of A and B is a hydroxyl group, the other of A and B is a hydrogen and when one of A and B is a halogen, the other of A and B is a halogen or a hydrogen;
wherein Z is, for example, an aryl moiety; and
wherein $X_1$ and $X_2$ are, for example, individually selected from a hydrogen and an alkyl moiety,
wherein $R_1$ and $R_2$ are individually selected from an oxo, a hydroxyl or an ester group;
wherein y is 0 or 1, x is 0 or 1 and x and y are not both 1, or a salt.

2 Claims, 1 Drawing Sheet

(56) References Cited

U.S. PATENT DOCUMENTS

| | | |
|---|---|---|
| 5,578,618 A | 11/1996 | Stjernschantz et al. |
| 5,607,978 A | 3/1997 | Woodward et al. |
| 5,627,208 A | 5/1997 | Stjernschantz et al. |
| 5,631,287 A | 5/1997 | Schneider |
| 5,665,773 A | 9/1997 | Klimko et al. |
| 5,688,819 A | 11/1997 | Woodward et al. |
| 5,834,498 A | 11/1998 | Burk |
| 5,849,791 A | 12/1998 | Stjernschantz et al. |
| 5,849,792 A | 12/1998 | Schneider |
| 5,886,035 A | 3/1999 | Shirasawa et al. |
| 5,889,052 A | 3/1999 | Klimko et al. |
| 5,977,173 A | 11/1999 | Wos et al. |
| 5,985,920 A | 11/1999 | Shirasawa et al. |
| 6,011,062 A | 1/2000 | Schneider et al. |
| 6,048,895 A | 4/2000 | Wos et al. |
| 6,107,338 A | 8/2000 | Wos et al. |
| 6,124,344 A | 9/2000 | Burk |
| 6,160,129 A | 12/2000 | Burk |
| 6,184,250 B1 | 2/2001 | Klimko et al. |
| 6,187,813 B1 | 2/2001 | Stjernschantz et al. |
| 6,235,781 B1 | 5/2001 | Weiner et al. |
| 6,248,783 B1 | 6/2001 | Burk et al. |
| 6,258,844 B1 | 7/2001 | Garst et al. |
| 6,262,105 B1 | 7/2001 | Johnstone |
| 6,291,522 B1 | 9/2001 | Burk |
| 6,307,092 B1 | 10/2001 | Burk et al. |
| 6,310,087 B2 | 10/2001 | Burk |
| 6,323,204 B1 | 11/2001 | Burke et al. |
| 6,342,524 B1 | 1/2002 | Hellberg et al. |
| 6,344,478 B2 | 2/2002 | Dean et al. |
| 6,359,181 B1 | 3/2002 | Burk et al. |
| 6,369,089 B1 | 4/2002 | Burk et al. |
| 6,372,730 B1 | 4/2002 | deLong et al. |
| 6,380,250 B1 | 4/2002 | Burk |
| 6,380,251 B1 | 4/2002 | Burk |
| 6,403,649 B1 | 6/2002 | Woodward et al. |
| 6,407,250 B1 | 6/2002 | Burk et al. |
| 6,410,591 B1 | 6/2002 | Burk et al. |
| 6,410,780 B1 | 6/2002 | deLong et al. |
| 6,414,022 B2 | 7/2002 | Burk |
| 6,417,230 B1 | 7/2002 | Stjernschantz |
| 6,429,226 B1 | 8/2002 | Stjernschantz et al. |
| 6,440,460 B1 | 8/2002 | Gurny et al. |
| 6,441,047 B2 | 8/2002 | DeSantis, Jr. |
| 6,444,840 B1 | 9/2002 | deLong et al. |
| 6,451,859 B1 | 9/2002 | deLong et al. |
| 6,476,064 B1 | 11/2002 | Old et al. |
| 6,486,208 B1 | 11/2002 | Castillo et al. |
| 6,509,364 B2 | 1/2003 | Burk et al. |
| 6,511,999 B2 | 1/2003 | Burk et al. |
| 6,531,504 B2 | 3/2003 | Burk et al. |
| 6,538,018 B1 | 3/2003 | Burk et al. |
| 6,573,294 B1 | 6/2003 | Old et al. |
| 6,573,390 B2 | 6/2003 | Burk |
| 6,602,900 B2 | 8/2003 | Burk |
| 6,627,210 B2 | 9/2003 | Olejnik et al. |
| 6,641,834 B2 | 11/2003 | Olejnik et al. |
| 6,646,001 B2 | 11/2003 | Hellberg et al. |
| 6,670,485 B2 | 12/2003 | Burk et al. |
| 6,673,337 B2 | 1/2004 | Olejnik et al. |
| 6,680,337 B2 | 1/2004 | Burk |
| 6,706,755 B2 | 3/2004 | Old et al. |
| 6,710,072 B2 | 3/2004 | Burk et al. |
| 6,713,268 B2 | 3/2004 | Woodward et al. |
| 6,716,864 B2 | 4/2004 | Burk et al. |
| 6,716,876 B2 | 4/2004 | Burk |
| 6,723,748 B2 | 4/2004 | Klimko et al. |
| 6,734,206 B1 | 5/2004 | Old et al. |
| 6,743,439 B1 | 6/2004 | Castillo et al. |
| 6,767,920 B2 | 7/2004 | Burk et al. |
| 6,787,517 B1 | 9/2004 | Gil et al. |
| 6,864,282 B2 | 3/2005 | Ling et al. |
| 6,875,787 B2 | 4/2005 | Donde |
| 6,894,175 B1 | 5/2005 | deLong |
| 6,906,097 B2 | 6/2005 | Old et al. |
| 6,956,057 B2 | 10/2005 | Woodward et al. |
| 6,989,445 B2 | 1/2006 | Dantanarayana et al. |
| 7,015,243 B2 | 3/2006 | Old et al. |
| 7,045,634 B2 | 5/2006 | Krauss et al. |
| 7,060,297 B2 | 6/2006 | Karakelle et al. |
| 7,070,768 B2 | 7/2006 | Krauss |
| 7,074,942 B2 | 7/2006 | deLong |
| 7,091,231 B2 | 8/2006 | Donde et al. |
| 7,101,904 B2 | 9/2006 | Donde et al. |
| 7,101,906 B2 | 9/2006 | Donde et al. |
| 7,115,659 B2 | 10/2006 | deLong |
| 7,129,257 B1 | 10/2006 | Dantanarayana et al. |
| 7,183,310 B2 | 2/2007 | Donde et al. |
| 7,183,324 B2 | 2/2007 | Donde et al. |
| 7,186,744 B2 | 3/2007 | Woodward et al. |
| 7,351,404 B2 | 4/2008 | Woodward et al. |
| 7,388,029 B2 | 6/2008 | DeLong et al. |
| 7,407,987 B2 | 8/2008 | deLong et al. |
| 7,521,530 B2 | 4/2009 | Peri et al. |
| 7,589,233 B2 | 9/2009 | Chandran |
| 7,879,910 B1 | 2/2011 | Marini |
| 2002/0013294 A1 | 1/2002 | deLong et al. |
| 2002/0037914 A1 | 3/2002 | deLong et al. |
| 2002/0045659 A1 | 4/2002 | Michelet et al. |
| 2002/0052414 A1 | 5/2002 | Bernard et al. |
| 2002/0146439 A1 | 10/2002 | DeLong et al. |
| 2002/0172693 A1 | 11/2002 | deLong et al. |
| 2003/0147823 A1* | 8/2003 | Woodward et al. .......... 424/70.1 |
| 2003/0165549 A1 | 9/2003 | Bernard et al. |
| 2003/0199590 A1 | 10/2003 | Cagle et al. |
| 2004/0082013 A1 | 4/2004 | Regan |
| 2004/0253202 A1 | 12/2004 | Chowhan et al. |
| 2004/0253280 A1 | 12/2004 | Chowhan et al. |
| 2005/0058614 A1 | 3/2005 | Krauss |
| 2005/0112075 A1 | 5/2005 | Hwang et al. |
| 2005/0130960 A1 | 6/2005 | Dantanarayana et al. |
| 2005/0171190 A1 | 8/2005 | May et al. |
| 2005/0222232 A1 | 10/2005 | deLong et al. |
| 2005/0239871 A1 | 10/2005 | Hellberg et al. |
| 2006/0106078 A1 | 5/2006 | Krauss et al. |
| 2006/0121069 A1 | 6/2006 | deLong et al. |
| 2006/0154981 A1 | 7/2006 | Klimko et al. |
| 2006/0182781 A1 | 8/2006 | Hughes et al. |
| 2006/0247214 A1 | 11/2006 | deLong et al. |
| 2007/0004620 A1 | 1/2007 | Jabbour et al. |
| 2008/0096240 A1 | 4/2008 | Woodward et al. |
| 2008/0103184 A1 | 5/2008 | deLong et al. |
| 2009/0286769 A1 | 11/2009 | DeLong et al. |
| 2011/0091405 A1 | 4/2011 | Marini |

FOREIGN PATENT DOCUMENTS

| | | |
|---|---|---|
| CN | 1522135 | 8/2004 |
| DE | 2517771 | 10/1976 |
| DE | 69823852 | 5/2005 |
| EP | 0093380 | 11/1983 |
| EP | 0572014 | 12/1993 |
| EP | 0925787 | 6/1999 |
| EP | 0857718 | 8/2002 |
| EP | 1267807 | 11/2005 |
| EP | 1267806 B1 | 12/2005 |
| FR | 2400895 | 3/1979 |
| GB | 2025413 | 1/1980 |
| JP | 60032718 | 2/1985 |
| JP | 61218510 | 9/1986 |
| JP | 03034934 | 2/1991 |
| JP | 3083925 | 4/1991 |
| JP | 5331025 | 12/1993 |
| JP | 7048345 | 2/1995 |
| JP | 7238037 | 9/1995 |
| JP | 8501310 | 2/1996 |
| JP | 8083926 | 3/1996 |
| JP | 8510734 | 11/1996 |
| JP | 10087607 | 4/1998 |
| JP | H10-287532 | 10/1998 |
| JP | 2001511155 | 8/2001 |
| JP | 2003180399 | 7/2003 |
| JP | 2003321442 | 11/2003 |
| WO | WO-8404917 | 12/1984 |

(56) References Cited

FOREIGN PATENT DOCUMENTS

| | | |
|---|---|---|
| WO | WO-9002553 | 3/1990 |
| WO | WO-9202496 | 2/1992 |
| WO | WO-9511003 | 4/1995 |
| WO | WO-9730710 | 8/1997 |
| WO | WO-9812175 | 3/1998 |
| WO | WO-9833497 | 8/1998 |
| WO | WO-9912895 | 3/1999 |
| WO | WO-9912896 | 3/1999 |
| WO | WO-9912898 | 3/1999 |
| WO | WO-9912899 | 3/1999 |
| WO | WO-9950242 | 10/1999 |
| WO | WO-0007627 | 2/2000 |
| WO | WO-0051979 | 9/2000 |
| WO | WO-0051980 | 9/2000 |
| WO | WO-0110873 | 2/2001 |
| WO | WO-02067901 | 9/2002 |
| WO | WO-03051822 | 6/2003 |
| WO | WO-03066008 | 8/2003 |
| WO | WO-03077910 | 9/2003 |
| WO | WO-2006106311 | 10/2006 |
| WO | WO-2007000642 | 1/2007 |
| WO | WO-2010096123 | 8/2010 |
| WO | WO-2010108012 | 9/2010 |

OTHER PUBLICATIONS

Invitation to Pay Additional Fees and Partial International Search for Application No. PCT/US2009/062590 (WO 2010/096123) dated Aug. 19, 2010, 5 pages.
International Search Report and Written Opinion for Application No. PCT/US2009/062590 (WO 2010/096123) dated Nov. 16, 2010, 16 pages.
Invitation to Pay Additional Fees and Partial International Search for Application No. PCT/US2010/43701 dated Sep. 28, 2010, 2 pages.
International Search Report and Written Opinion for Application No. PCT/US2010/43701 dated Dec. 7, 2010, 10 pages.
International Search Report and Written Opinion for Application No. PCT/US2010/27831 (WO 2010/108012) dated Apr. 26, 2010, 8 pages.
"Abstracts", Investigative Ophthalmology & Visual Science, A Journal of Clinical and Basic Research, Mar. 1982, vol. 22/3, ©1882 by the Association of Research in Vision and Ophthalmology, Inc., 3A-6A.
"Bimatoprost (Ophthalmic)", Drug information retrieved from www.drugs.com on Aug. 14, 2008, 4 pages.
"Chloprostenol", The Merck Index an Encyclopedia of Chemicals, Drugs, and Biologicals, Eleventh Edition, 1989 (2399), 378.
"Fluprostenol", The Merck Index an Encyclopedia of Chemicals, Drugs, and Biologicals, Eleventh Edition, 1989 (4117), 686-687.
"New Antithrombotic Agents", Abstracts, XVIth Congress of the International Society on Thrombosis and Haemostasis, Schattauer, Florence, Italy, (693), Jun. 11, 1997.
"Phase III Lumigan—AGN 192024—Data Presented at American Academy of Ophthalmology", Business Wire, (Oct. 23, 2000), 3 pages.
Abramovitz, Mark, et al., "Cloning and Expression of a cDNA for the Human Prostanoid FP Receptor", The Journal of Biological Chemistry, vol. 269, No. 4, (Jan. 28, 1994), 2632-2636.
Abramovitz, Mark, et al., "The utilization of recombinant prostanoid receptors to determine the affinities and selectivities of prostaglandins and related analogs", Biochimica et Biophysica Acta (BBA)—Molecular and Cell Biology of Lipids, vol. 1483, Issue 2, (Jan. 17, 2000), Abstract.
Adis Data Information BV, "ZD 6416 clinical information", AstraZeneca, (2006), 1 page.
Allergan, Inc., Allergan Clinical Study Report, Study No. 192024-010-01, A multi-center, investigator-masked, randomized, parallel study of the safety and efficacy of AGN 192024 0.03% ophthalmic solution compared with Latanoprost 0.005% ophthalmic solution administered o, (May 9, 2001), 38 pages.
Allergan, Inc., Allergan Clinical Study Report, Study No. 192024-009, A multicenter, double-masked, randomized, parallel 3-month study (with treatment extended to 1 year) of the safety and efficacy of AGN 192024 0.03% ophthalmic solution administered once-daily or twice-, (Aug. 2, 2000), 34 pages.
Allergan, Inc., "Lumigan product information insert", (Jun. 2006), 2 pages.
Alm, Albert, et al., "Effects on Intraocular Pressure and Side Effects of 0.005% Latanoprost Applied Once Daily, Evening or Morning", Ophthalmology, vol. 102, (1995), 1743-1752.
Alm, Albert, et al., "Phase III Latanoprost Stuides in Scandinavia, the United Kingdom and the United States", Survey of Ophthalmology, vol. 41, Suppl. 2, (Feb. 1997), S105-S110.
Al-Sereiti, M, et al., "Pharmacology of rosemary (*Rosmarinus officinalis* Linn.) and its therapeutic potentials", Indian Journal of Experimental Biology, vol. 37, (Feb. 1999), 124-130.
Athena Cosmetics, Non-Final Office Action mailed Mar. 28, 2012 for U.S. Appl. No. 12/698,823., 9 pages.
Athena Cosmetics Corporation, International Preliminary Report on Patentability dated Jan. 28, 2010 for PCT/US2008/007537.
Athena Cosmetics Corporation, PCT International Search Report and Written Opinion (dated Sep. 22, 2009), International Application No. PCT/US2008/007537, 13 pages.
Athena Cosmetics, Inc., Invitation to pay additional fees with partial international search dated May 27, 2011 for PCT/US2010/044170.
Athena Cosmetics, Inc., PCT Search Report and Written Opinion dated Aug. 17, 2011 for PCT/US2010/044170, 17 pages.
Audoly, L., et al., "Identification of specific EP receptors responsible for the hemodynamic effects of PGE2", The American Physiological Society, 277 (Heart Circ. Physiol. 46), (1999), H924-H930.
Badawy, S. I., et al., "Salt selection for pharmaceutical compounds", Preformulation in Solid Dosage Form Development, Adeyeye, J. editor, Informa Healthcare, Chapter 2.3, (2008), 63-80.
Bannai, K., et al., "Syntheses and their biological activities of fluorinated prostaglandins", Inst. Bio-Med. Res., Yuki Gosei Kagaku Kyokaishi; 42(9); Coden:YGKKAE ISSN: 0372-770X; Journal; General; Review written in Japanese, (1984), 794-808.
Bartman, W., et al., "Luteolytic prostaglandins synthesis and biological activity", Prostaglandins, vol. 17, No. 2, (Feb. 1979), 301-311.
Bastin, R. J., et al., "Salt selection and optimisation procedures for pharmaceutical new chemical entities", Organic Process R&D, 4(5), (2000), 427-435.
Begue, Jean-Pierre, et al., "Biological Impacts of Fluorination: Pharmaceuticals Based on Natural Products", Fluorine and Health, Chapter 13, Elsevier B.V., (2008), 553-622.
Begue, Jean-Pierre, et al., "Recent Advances (1995-2005) in fluorinated pharmaceuticals based on natural products", Journal of Fluorine Chemistry, vol. 127, (2006), 992-1012.
Begue, Jean-Pierre, et al., "Recent Advances (1995-2005) in Fluorinated Pharmaceuticals based on Natural Products", Journal of Fluorine Chemistry 127, (2006), pp. 992-1012.
Berge, S. M., et al., "Pharmaceutical salts", J. Pharm. Sci., 66(1), (1997), 1-19.
Bezuglov, V. V., et al., "Reaction of prostaglandin F2α antiserum to some modified F2 prostaglandins", Inst. Bioorg. Khim. im. Shemyakina, Moscow, USSR; Doklady Akademii Nauk SSSR, 255(4) [Biochem.]; Coden: DANKAS ISSN: 0002-3264; Journal written in Russian; Abstract, (1980), 999-1002.
Bezuglov, V. V., et al., "Synthesis of fluoro prostaglandins. I. 11-fluoro and 15-fluoro prostaglandins", Bioorganicheskaya Khimiya, 5(10); Coden: BIKHD7 ISSN: 0132-3423; Journal written in Russian; Abstract, (1979), 1531-6.
Bito, Laszlo Z., et al., "Eicosanoids as a New Class of Ocular Hypotensive Agents. 1. The Apparent Therapeutic Advantages of Derived Prostaglandins of the A and B Type as Compared with Primary Prostaglandins of the E, F and D Type", Experimental Eye Research, vol. 44, Issue 6, Jun. 1987, 825-837.
Bito, L. Z., et al., "Long-term Maintenance of Reduced Intraocular Pressure by Daily or Twice Daily Topical Application of Prostaglandins to Cat or Rhesus Monkey Eyes", Invest Ophthalmol Vis Sci, vol. 24, (1983), 312-319.
Bito, et al., "Maintenance of reduced intraocular pressure (IOP) for several months by topical application of prostaglandin (PG) to eyes of trained cats", Investigative Ophthalmology and Visual Science, vol. 22, No. 3, (Mar. 1982), 39.

(56) References Cited

OTHER PUBLICATIONS

Bito, et al., "The ocular effects of prostaglandins and the therapeutic potential of a new PGF2 analog, PhXA41 (latanoprost), for glaucoma management", Journal of Lipid Mediators, vol. 6, No. 1-3, (1993), 535-543.
Brandt, James D., et al., "Comparison of Once- or Twice-daily Bimatoprost with Twice-daily Timolol in Patients with Elevated IOP", Ophthalmology, vol. 108, (2001), 1023-1032.
Brubaker, Richard F., et al., "Effects of AGN 192024, a New Ocular Hypotensive Agent, on Aqueous Dynamics", Am J Ophthalmol, vol. 131, (Jan. 2001), 19-24.
Bundy, G., et al., "Synthesis of 17-phenyl-18,19,20-trinorprostaglandins: I. The PG1 series", Prostaglandins, vol. 9, No. 1, (Jan. 1975), 1-4.
Camras, Carl B., "Comparison of Latanoprost and Timolol in Patients with Ocular Hypertension and Glaucoma", Ophthalmology, vol. 103, No. 1, (1996), 138-147.
Camras, Carl B., et al., "Intraocular Pressure Reduction With PhXA34, a new Prostaglandin Analogue, in Patients With Ocular Hypertension", Arch Ophthalmol., vol. 110, (Dec. 1992), 1733-1738.
Camras, Carl B., et al., "Latanoprost, a Prostaglandin Analog, for Glaucoma Therapy", Ophthalmology, vol. 103, No. 11, (1996), 1916-1924.
Camras, Carl B., et al., "Multiple Dosing of Prostaglandin F2alpha or Epinephrine on Cynomolgus Monkey Eyes", Invest Ophthalmol Vis Sci, vol. 28, No. 3, (1987), 463-469.
Camras, Carl B., et al., "Multiple Dosing of Prostaglandin F2alpha or Epinephrine on Cynomolgus Monkey Eyes", Invest Ophthalmol Vis Sci, vol. 28, No. 6, (1987), 921-926.
Camras, Carl B., et al., "Multiple Dosing of Prostaglandin F2alpha or Epinephrine on Cynomolgus Monkey Eyes", Invest Ophthalmol Vis Sci, vol. 29, No. 9, (1988), 1428-1436.
Camras, Carl B., et al., "Reduction of intraocular pressure by prostaglandins applied topically to the eyes of conscious rabbits", Investigative Ophthalmology & Visual Science, Dec. 1997, vol. 16/12, 1125-1134.
Cayatte, Antonio J., et al., "The Thromboxane Receptor Antagonist S18886 but Not Aspirin Inhibits Atherogenesis in Apo E-Deficient Mice: Evidence That Eicosanoids Other Than Thromaboxane Contribute to Atherosclerosis", Arterioscler. Thromb. Vasc. Biol., vol. 20, (2000), 1724-1728.
Cayman Chemical, Tafluprost product information, Catalog No. 10005440; CAS Registry No. 209860-87-87, (Dec. 1, 2007), 1 page.
Chyun, Y. S., et al., "Stimulation of bone formation by prostaglandin E2", Prostaglandins, vol. 27, No. 1, (Jan. 1984), Abstract.
Coleman, Robert A., et al., "Prostanoids and their Receptors", Comprehensive Medicinal Chemistry, Pergamon Press, Oxford (1990), 643-714.
Coleman, R., et al., "VIII. International union of pharmacology classification of prostanoid receptors: properties, distribution, and structure of the receptors and their subtypes", Pharmacology Reviews, vol. 46, No. 2, (1994), 206-229.
Corsini, A., et al., "(5Z)-carbacyclin discriminates between prostacyclin-receptors coupled to adenylate cyclase in vascular smooth muscle and platelets", Br. J. Pharmac., vol. 90, (1987), 255-261.
Darnell, J., et al., "Cell-to-Cell Signaling: Hormones and Receptors", Molecular Cell Biology, W.H. Freeman and Company, New York, New York, (1990), 738-743.
Del Toro, Jr., F, et al., "Characterization of Prostaglandin E2 Receptors and Their Roll in 24,25-(OH)2D3-Mediated Effects on Resting Zone Chondrocytes", Journal of Cellular Physiology, vol. 182, No. 2, Feb. 2000, ISSN: 0021-9541, 198-208.
DeLong, Mitchell A., "Prostaglandins receptor ligands: Recent patent activity", IDrugs, vol. 3(9), (2000), 1039-1052.
Eisenberg, D. L., et al., "A preliminary risk-benefit assessment of latanoprost and unoprostone in open-angle glaucoma and ocular hypertension", Drug Saf., vol. 20, No. 6, (Jun. 1999), Abstract.

Ellis, C, et al., "Metabolism of prostaglandin D2 in the monkey", Journal of Biological Chemistry, vol. 254, Issue 10, (May 1979), 4152-4163.
Fagot, Dominique, et al., "Mitogenic Signaling by Prostaglandins in Chemically Transformed Mouse Fibroblasts: Comparison with Phorbol Esters and Insulin", Endocrinology, vol. 132, (1993), 1729-1734.
Fall, P., et al., "Inhibition of collagen synthesis by prostaglandins in the immortalized rat osteoblastic cell line pyla:structure-activity relations and signal transduction mechanisms", J Bone Miner Res, 9(12), (Dec. 1994), 1935-1943.
Fitzpatrick, F. , "Separation of prostaglandins and thromboxanes by gas chromatography with glass capillary columns", Analytical Chemistry, vol. 50, No. 1, (Jan. 1978), 47-52.
Flisiak, R., et al., "Effect of misoprostol on serum beta2-microglobulin in the course of viral hepatitis B", European Journal of Gastroenterology and Hepatology, vol. 11, No. 11, (1999), Abstract.
Funk, Colin D., et al., "Cloning and Expression of a cDNA for the Human Prostaglandin E Receptor EP1 Subtype*", The Journal of Biological Chemistry, vol. 268, No. 35, (Dec. 15, 1993), 26767-26772.
Geng, L., et al., "Topical or systemic 16, 16 dm prostaglandin E2 or WR-2721 (WR-1065) protects mice from alopecia after fractionated irradiation", Int J Radiat Biol., vol. 61, No. 4, (Apr. 1996), Abstract.
Giuffre, Giuseppe , "The effects of prostaglandin F2alpha in the human eye", Graefe's Arch Clin Exp Ophthalmol, vol. 222, (1985), 139-141.
Glass, Michelle, et al., "Misidentification of prostamides as prostaglandins", Journal of Lipid Research, vol. 46, (Jul. 2005), 1364-1368.
Goldberg, et al., "Dipivefrin: current concepts", Australian Journal of Ophthalmology, 8, (1980), 147-150.
Grieco, Paul A., et al., "C(14)-Fluorinated Prostaglandins: Synthesis and Biological Evaluation of the Methyl Esters of (+)-14-Fluoro-, (+)-15-epi-14-Fluoro-, (+)-13(E)-14- Fluoro-, and (+)-13(E)-15-epi-14-Fluoroprostaglandin F2alpha", J. Med. Chem., vol. 23, (1980), 1077-1083.
Grieco, Paul A., et al., "Ring-Fluorinated Prostaglandins: Total Synthesis of (+−)-10alpha-Fluoroprostaglandin F2alpha Methyl Ester", J. Org. Chem., vol. 44, No. 13, (1979), 2194-2199.
Griffin, Brenda W., et al., "AL-8810: A Novel Prostaglandin F2alpha Analog with Selective Antagonist Effects at the Prostaglandin F2alpha (FP) Receptor", The Journal of Pharmacology and Experimental Therapeutics, vol. 290, No. 3, (1999), 1278-1284.
Hallinan, E. A., et al., "Aminoacetyl Moiety as a Potential Surrogate for Diacylhydrazine Group of SC-51089, a Potent PGE2 Antagonist, and Its Analogs", J. Med. Chem., vol. 39 (2), (1996), Abstract.
Hanson, W. R., et al., "16, 16-dimethyl prostaglandin E2 increases survival of murine intestinal stem cells when given before photon radiation", Radiat Res., vol. 96, No. 2, (Nov. 1983), Abstract.
Hanson, W. R., et al., "Subcutaneous or topical administration of 16,16 dimethyl prostaglandin E2 protects from radiation-induced alopecia in mice", Int. J. Radiat. Oncol. Biol. Phys., vol. 23(2), (1992), Abstract.
Hayashi, M., et al., "Prostaglandin Analogues Possessing antinidatory effects. 1. Modifications of the ω chain", J. Med. Chem., 23, (1980), 519-524.
Houssay, Alberto B., et al., "Effects of Prostaglandins Upon Hair Growth in Mice", Acta Physiol Latinoam, vol. 26, (1976), 186-191.
Hulan, H. W., et al., "The development of dermal lesions and alopecia in male rats fed rapeseed oil", Can. J. Physiol. Pharmacol., vol. 54(1), (Feb. 1976), Abstract.
Hulan, H. W., et al., "The Effect of Long-Chain Monoenes on Prostaglandin E2 Synthesis by Rat Skin", Lipids, vol. 12, No. 7, (1977), 604-609.
Ichikawa, A., et al., "Molecular aspects of the structures and functions of the prostaglandin E receptors", Journal of Lipid Mediators and Cell Signalling, vol. 14, Issues 1-3, (Sep. 1996), Abstract.
Informa UK Ltd., "Bimatoprost clinical information", (2006), 3 pages.
Informa UK Ltd., "Pharmaprojects No. 6321 clinical information", Merck & Co., (2006), 1 page.

(56) References Cited

OTHER PUBLICATIONS

Jakobsson, Per-Johan, et al., "Membrane-associated Proteins in Eicosanoid and Glutathione Metabolism (MAPEG): A Widespread Protein Superfamily", Am J Respir Crit Care Med, vol. 161, (2000), S20-S24.

Jiang, H., et al., "Induction of anagen in telogen mouse skin by topical application of FK506, a potent immunosuppressant", J Invest Dermatol., vol. 104, No. 4, (Apr. 1995), Abstract.

Jimenez De Asua, L., et al., "The Stimulation of the Initiation of DNA Synthesis and Cell Division in Swiss Mouse 3T3 Cells by Prostaglandin F2alpha Requires Specific Functional Groups in the Molecule", J Biol Chemistry, vol. 256, No. 14, (1983), 8774-8780.

Johnstone, M. A., "Hypertrichosis and increased pigmentation of eyelashes and adjacent hair in the region of the ipsilateral eyelids of patients treated with unilateral topical latanoprost", Am J Ophthalmol., vol. 124, No. 4, (Oct. 1997), Abstract.

Kass, M., et al., "Dipivefrin and epinephrine treatment of elevated intraaocular pressure", Arch Ophthalmol, vol. 97, (Oct. 1979), 1865-1866.

Kass, M., et al., "Prostaglandin E1 and aqueous humor dynamics", Investigative Ophthalmology, vol. 11, No. 12, (Dec. 1972), 1022-1027.

Kaufman, Paul L., "Effects of Intracamerally Infused Prostaglandins on Outflow Facility in Cynomolgus Monkey Eyes with Intact or Retrodisplaced Ciliary Muscle", Exp Eye Res, vol. 43, (1986), 819-827.

Kaye, B. H., "Science and the Detective", Arzneimittel Forschung Drug Research, Special Section: Biotechnology in Drug Research, vol. 45 (ii), No. 9, 1995, ISSN 0004-4172, 941-1048.

Kende, A., et al., "Prostaglandin phosphonic acids through homolytic halodecarboxylation of prostaglandins F1$\alpha$ and F2$\alpha$", Tetrahedron Letters, 40, (1999), 8189-8192.

Kerstetter, J R., et al., "Prostaglandin F2$\alpha$-1-Isopropylester Lowers Intraocular Pressure Without Decreasing Aqueous Humor Flow", American Journal of Ophthalmology, vol. 105, No. 1, Jan. 1988, 30-34.

Kiriyama, Michitaka, et al., "Ligand binding specificities of the eight types and subtypes of the mouse prostanoid receptors expressed in Chinese hamster ovary cells", British Journal of Pharmacology, vol. 122, (1997), 217-224.

Kluender, H., et al., "The synthesis of dimethylphosphonoprostaglandin analogs", Prostaglandins and Medicine, 2, (1979), 441-444.

Krauss, Achim H., et al., "Evidence for human thromboxane receptor heterogeneity using a novel series of 9,11-cyclic carbonate derivatives of prostaglandin F2alpha", British Journal of Pharmacology, vol. 117, (1996), 1171-1180.

Kvedar, J. C., et al., "Topical minoxidil in the treatment of male pattern alopecia", Pharmacotherapy, vol. 7, No. 6, (1987), Abstract.

Lachgar, S , "Effect of VEGF and minoxidil on the production of arachidonic acid metabolites by cultured hair, dermal papilla cells", Eur J Dermatol, vol. 6, (1996), 365-368.

Lakin, K. M., et al., "The effect of fluorinated prostaglandins on platelet aggregation", Eksperimental'naya i Klinicheskaya Farmakologiya, 57(2), (1994), 39-41.

Lardy, C., et al., "Antiaggregant and antivasospastic properties of the new thromboxane A2 receptor antagonist sodium 4-[[1-[[[(4-chlorophenyl)sulfonyl]amino]methyl]cyclopentyl] methyl]benzeneacetate", Arzneimittelforschung, vol. 44, No. 11, (Nov. 1994), Abstract.

Lee, Ping-Yu, et al., "The Effect of Prostaglandin F2alpha on Intraocular Pressure in Normotensive Human Subjects", Invest Ophthalmol Vis Sci, vol. 29, (1988), 1474-1477.

Liljebris, C., et al., "Derivatives of 17-phenyl-18,19,20-trinorprostaglandin F2_alpha isopropyl ester: potential antiglaucoma agents", J. Med. Chem., 38, (1995), 289-304.

Malkinson, Frederick D., et al., "Prostaglandins Protect Against Murine Hair Injury Produced by Ionizing Radiation or Doxorubicin", J. Invest. Dermatol., vol. 101, (1993), 135S-137S.

Mansberger, S. L., et al., "Eyelash formation secondary to latanoprost treatment in a patient with alopecia", Arch. Ophthalmol. 118, (2000), 718-719.

Matsumura, Y., et al., "Recent developments in fluorinated prostanoids", Journal of Synthetic Organic Chemistry, Japan, vol. 63, No. 1, (2005), 42-52.

Matsumura, Yasushi , "Synthesis and Pharmacological Properties of Fluorinated Prostanoids", Fluorine and Health, Chapter 14, Elsevier B.V., (2008), 623-659.

Michelet, Jean-Francois, et al., "Activation of Cytoprotective Prostaglandin Synthase-1 by Minoxidil as a Possible Explanation for Its Hair Growth-Stimulating Effect", J. Invest. Dermatol., vol. 108, (1997), 205-209.

Mihele, Denisa, et al., "*Cercetarea actiunii* Hepatoprotectoare a Unor Prostaglandine de Sinteză", Farmacia, vol. XLCVII, Nr. 5, Septembrie-Octombrie 1999, ISSN 0014-8237, 43-58.

Mishima, Hiromu K., et al., "A Comparison of Latanoprost and Timolol in Primary Open-angle Glaucoma and Ocular Hypertension", Arch Ophthalmol, vol. 114, (1996), 929-932.

Miyamoto, Terumasa, et al., "A Comparison in the Efficacy and Safety between Ramatroban (BAY u 3405) and Ozagrel HCl for Bronchial Asthma", A Phase III, Multi-Center, Randomized, Double-Blind, group Comparative Study, 1997, 600(92)-639(131).

Mori, S., et al., "Effects of prostaglandin E2 on production of new cancellous bone in the axial skeleton of ovariectomized rats", Bone, vol. 11, No. 2, (1990), Abstract.

Murakami, T., et al., "Effect of isocarbacyclin methyl ester incorporated in lipid microspheres on experimental models of peripheral ostructive disease", Arzneim. Fosch/Drug Res., 45(11), (1995), 991-994.

Narumiya, S. , "Roles of prostanoids in health and disease; lessons from receptor-knockout mice", Common Disease: Genetic and Pathogenetic Aspects of Multifactorial Diseases, Uehara Memorial Foundation Symposium, (1999), 261-269.

Narumiya, Shuh, et al., "Structure and function of prostanoid receptors", Journal of Lipid Mediators, Mar.-Apr. 1993, vol. 6 (1-3), 155-161.

Neau, S. H., "Pharmaceutical salts", Water-Insoluble Drug Formulation, Rong Liu editor, CRC Press, 15, (2008), 417-435.

Negishi, M., et al., "Molecular mechanisms of diverse actions of prostanoid receptors", Biochim-biophys-acta, Amsterdam, Elsevier Science B.V., vol. 1259 (1), (Oct. 26, 1995), Abstract.

Olsen, E. A., et al., "Transdermal viprostol in the treatment of male pattern baldness", J Am Acad Dermatol., vol. 23, No. 3, Pt. 1, (Sep. 1990), Abstract.

Orlicky, D. J., "Negative regulatory activity of a prostaglandin F2alpha receptor associated protein (FPRP)", Prostaglandins, Leukotrienes and Essential Fatty Acids, vol. 54, Issue 4, (Apr. 1996), Abstract.

O'Toole, et al., "Eyelid hypertrichosis associated with Latanoprost is reversible", European Journal of Ophthalmology, vol. 11, N. 4, (2001), 377-379.

Rampton, D., et al., "Anti-inflammatory profile in vitro of ridogrel, aputative new treatment for inflammatory bowel disease", Gastroenterology, G3477; vol. 116, No. 4, Part 2, (Apr. 1999), A301.

Resul, B , "Phenyl-substituted prostaglandins: potent and selective antiglaucoma agents", J. Med. Chem., 36, (1993), 243-248.

Resul, Bahram, et al., "Structure-Activity Relationships and Receptor Profiles of Some Ocular Hypotensive Prostanoids", Survey of Ophthalmology, vol. 41, Suppl. 2, (Feb. 1997), S47-S52.

Ruel, Rejean, et al., "New class of biphenylene dibenzazocinones as potent ligands for the human EP1 prostanoid receptor", Bioorganic & Medicinal Chemistry Letters, vol. 9, Issue 18, (Sep. 20, 1999), Abstract.

Ruel, R., et al., "New class of biphenylene dibenzazocinones as potent ligands for the human ep1 prostanoid receptor", Bioorganic & Medicinal Chemistry Letters, 9, (1999), 2699-2704.

Rundle, R. L., "Drug that lengthens eyelashes sets off flutter", URL:http://online.wsj.com/article/SB119543055372597359.html, (Nov. 19, 2007), 3 pages.

Sakuma, Yoko, et al., "Crucial Involvement of the EP4 Subtype of Prostaglandin E Receptor in Osteoclast Formation by Proinflamma-

(56) References Cited

OTHER PUBLICATIONS tory Cytokines and Lipopolysaccharide", Journal of Bone and Mineral Research, vol. 15, No. 2, (2000), 218-227.
Sauk, Jr., John J., et al., "Influence of Prostaglandins E1, E2, and Arachidonate on Melanosomes in Melanocytes", The Journal of Investigative Dermatology, vol. 64, No. 5, (1975), 332-337.
Serkov, I. V., et al., "Prostaglandin Fluorides in Synthesis of Natural Prostaglandin Derivatives at Carboxyl Group", Russian Journal of Bioorganic Chemistry, vol. 35, No. 1, (2009), 111-117.
Sharif, N. A., et al., "[3H]AL-5848 ([3H]9β-(+)-Fluprostenol. Carboxylic acid of travoprost (AL-6221), a novel FP prostaglandin o study the pharmacology and autoradiographic localization of the FP receptor", Journal of Pharmacy and Pharmacology, vol. 51, No. 6, (1999), Abstract.
Sharif, Najam A., et al., "Bimatoprost and its free acid are prostaglandin FP receptor agonists", European Journal of Pharmacology, vol. 432, (2001), 211-213.
Shih, M. S., et al., "PGE2 induces regional remodeling changes in haversian envelope: a histomorphometric study of fractured ribs in beagles", Bone Miner., vol. 1, No. 3, (Jun. 1986), Abstract.
Shimazaki, A., et al., "Effects of the new ethacrynic acid derivative SA9000 on intraocular pressure in cats and monkeys", Biol. Pharm. Bull., 27(7), (2004), 1019-1024.
Shimazaki, A., et al., "New ethacrynic acid derivatives as potent cytoskeletal modulators in trabecular meshwork cells", Biol. Pharm. Bull., 27(6), (2004), 846-850.
Sredni, B., et al., "The protective role of the immunomodulator AS101 against chemotherapy-induced alopecia studies on human and animal models", Int J Cancer, vol. 65, No. 1, (Jan. 1996), Abstract.
Stahl, P. H., et al., Handbook of Pharmaceutical Salts, Properties, Selection and Use, Wiley-Vch, Chapter 12, (2008), 265-327.
Starr, M., "Further studies on the effect of prostaglandin on intraocular pressure in the rabbit", Exp. Eye Res., 11, (1971), 170-177.
Stjernschantz, J, et al., "Latanoprost as a new horizon in the medical management of glaucoma", Current Opinion in Ophthalmology, 7(2), (1996), 11-17.
Stjernschantz, Johan, et al., "Phenyl substituted prostaglandin analogs for glaucoma treatment", Correlates in Pharmacostructures, Drug Future 17 (1992), 691-704.
Swarbrick, J., et al., Encyclopedia of Pharmaceutical Technology, Marcel Dekker, Inc., 13, (1988), 453-499.
Takagi, Yasutaka, "Pharmacological characteristics of AFP-168 (tafluprost), a new prostanoid FP receptor agonist, as an ocular hypotensive drug", Experimental Eye Research, vol. 78, (2004), 767-776.
Terada, N., et al., "Effect of a thromboxane A2 receptor antagonist, ramatroban (BAY u 3405), on inflammatory cells, chemical mediators and non-specific nasal hyperreactivity after allergen challenge in patients with perennial allergic rhinitis", Allergology International, 47, (1998), 59-67.
Tomita, Y., et al., "Melanocyte-stimulating properties of arachidonic acid metabolites: possible role in postinflammatory pigmentation", Pigment Cell Res., vol. 5, No. 5, Pt. 2, (Nov. 1992), Abstract.

Toris, C. B., et al., "Effects of PhXA41, a new prostaglandin F2 alpha analog, on aqueous humor dynamics in human eyes", Ophthalmology, vol. 100, No. 9, (Sep. 1993), Abstract.
Uno, Hideo, et al., "Effect of latanoprost on hair growth in the bald scalp of the stump-tailed macacque: A pilot study", Acta dermatovenereologica, vol. 82, No. 1, (2002), Abstract.
US Food and Drug Administration, "FDA Approves Two New Intraocular Pressure Lowering Drugs for the Management of Glaucoma", FDA News, http://fda/gov/bbs/topics/NEWS/2001/NEW00757.html, (Mar. 16, 2001), 2 pages.
Vayssairat, M., "Preventive effect of an oral prostacyclin analog, beraprost sodium, on digital necrosis in systemic schlerosis", The Journal of Rheumatology, vol. 26, No. 10, (Oct. 1999), 2173-2178.
Villumsen, Jorgen, et al., "Prostaglandin F2α-isopropylester eye drops: effect on intraocular pressure in open-angle glaucoma", British Journal of Ophthalmology, 1989, vol. 73, 975-979.
Villumsen, J, et al., "The Effect of Prostaglandin . . . Drops in Open Angle Glaucoma", 5-2.00, Investigative Ophthalmology and Visual Science, 1984, ARVO Abstract, 378.
Waddell, K., et al., "Combined capillary column gas chromatography negative ion chemical ionization mass spectrometry of prostanoids", Biomedical Mass Spectrometry, vol. 10, No. 2, (1983), 83-88.
Wang, Y., et al., "Design and synthesis of 13, 14-dihydro prostaglandin F(1alpha) analogues as potent and selective ligands for the human FP receptor", J Med Chem., vol. 43, No. 5, (Mar. 9, 2000), Abstract.
Waterbury, L., et al., "EP3, but not EP2, FP, or TP prostanoid-receptors stimulation may reduce intraocular pressure", Invest Ophthalmol Vis Sci, 31, (1990), 2560-2567.
Wax, Martin B., "Alternative and Future Medical Therapy of Glaucoma", Chapter 28, The Glaucomas, ©1989 by the C.V. Mosby Company, ISBN: 0-08016-4116-0, 557-564.
Woodward, D., "Emerging evidence for additional prostanoid receptor subtypes", Current Topics in Pharmacology, vol. 4, (1998), 153-162.
Woodward, David F., et al., "Intraocular pressure effects of selective prostanoid receptors agonists involve different receptor subtypes according to radioligand binding studies", Journal of Lipid Mediators, Mar.-Apr. 1993, vol. 6 (1-3), 545-553.
Woodward, David F., et al., "Molecular characterization and ocular hypotensive properties of the prostanoid EP2 receptor", J Ocul Pharmacol Ther., vol. 11, No. 3, (Fall 1995), Abstract.
Yu, J., et al., "Human hair keratins", The Society for Investigative Dermatology, Inc., vol. 101, No. 1, Supplement, (Jul. 1993), 56S-59S.
Zajacz, M, et al., "Effect on Human Eye of Prostaglandin and a Prostaglandin Analogue Used to Induce Abortion", IRCS Medical Science, Clinical Medicine: Clinical Pharmacology and Therapeutics: Drug Metabolism and Toxicology: The Eye: Reproduction, Obstetrics and Gynecology, vol. 4 (1976), 316.
Ziai, Niloofar, et al., "The Effects on Aqueous Dynamics of PhXA41, a New Prostaglandin F2alpha Analogue, After Topical Application in Normal and Ocular Hypertensive Human Eyes", Arch Ophthalmol., vol. 111, (Oct. 1993), 1351-1358.
Pharma Patent Holding Inc., Australian Examination Report dated Sep. 20, 2013 for AU Application No. 2010358560 1.

* cited by examiner

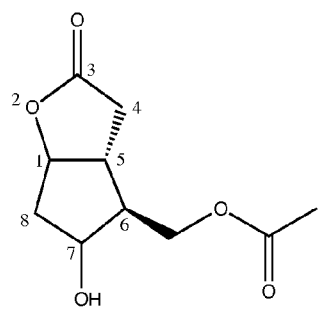
Corey acetate Derivative
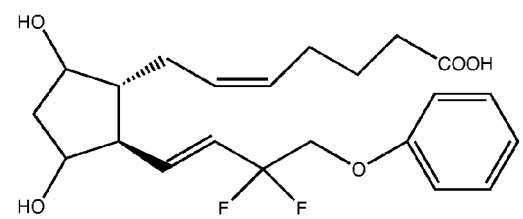
3,3,-difluoro-4-phenoxybut-1-enyl-3,5-dihydroxycyclopentyl-hept-5-enoic acid
Iodomethane, THF
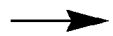
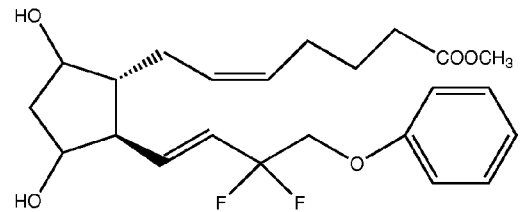
3,3,-difluoro-4-phenoxybut-1-enyl-3,5-dihydroxycyclopentyl-methyl-hept-5-enoate
Ethylamine in water
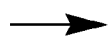
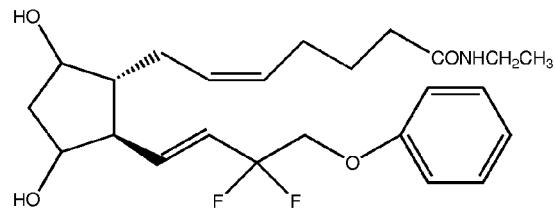
3,3,-difluoro-4-phenoxybut-1-enyl-3,5-dihydroxycyclopentyl-N-ethylhept-5-enamide

COMPOSITION, METHOD AND KIT FOR ENHANCING HAIR

CROSS-REFERENCE TO RELATED APPLICATION

The application is a continuation of U.S. patent application Ser. No. 12/698,823, filed Feb. 2, 2010, which claims the benefit of the earlier filing date of U.S. Provisional Patent Application No. 61/149,661, filed Feb. 3, 2009 and incorporated herein by reference.

FIELD

Composition, method and kit for enhancing human hair including eyelashes.

BACKGROUND

Certain therapeutic agents have been known to induce hair growth. One example is Minoxidil, 6-(1-piferidinyl)-2,4-pyrimidane-diamine 3-oxide (U.S. Pat. Nos. 3,382,247 and 3,644,363). Minoxidil was originally prepared and sold for use as an antihypertensive. It was observed that, associated with the use of Minoxidil for this latter purpose, Minoxidil use also produced an increase in hair growth and thickness as reported in U.S. Pat. Nos. 4,139,619 and 4,968,812. Today, Minoxidil is marketed under the trademark Rogaine® by Pfizer for the treatment of baldness on the scalp for men (alopecia androgenetica) and women. Another example is finasteride (Propecia®), marketed by Merck & Co. Finasteride was originally developed for benign prostatic hypertrophy, and was found to be effective in the treatment of alopecia androgenetica as reported in U.S. Pat. No. 4,968,812.

Among the drugs introduced for lowering intraocular pressure are molecules of the family prostaglandin F2. The Upjohn Company identified a prostaglandin F2α analog, commonly known as Latanoprost and whose chemical name is isopropyl-(Z)-7[(1R,2R,3R,5S)3,5-dihydroxy-2-[(3R)-3-hydroxy-5-phenylp-entyl]cyclopentyl]-5-heptenoate. Latanoprost is marketed by Pharmacia & Upjohn (currently a part of Pfizer) under the trademark Xalatan® for the reduction of elevated intraocular pressure in patients with glaucoma and ocular hypertension. The form is a Latanoprost optical solution of 0.005% (50 µg/ml), and is applied by dropper directly onto the eye. One drop generally contains approximately 1.5 µg of Latanoprost.

In the course of its use for reduction of intraocular pressure, Latanoprost has been reported to cause, in some patients, an increasing pigmentation and growth of eyelashes. U.S. Pat. No. 6,262,105 stated that the use of Latanoprost leads to increased length of lashes, increased numbers of lashes along the normal lash line, increased thickness and luster of lashes, increased auxiliary lash-like terminal hair in transitional areas adjacent to areas of normal lash growth, increased lash-like terminal hairs at the medial and lateral canthal area, increased pigmentation of the lashes, increased numbers, increased length, as well as increased luster, and thickness of fine hair on the skin of the adjacent lid, and increased perpendicular angulation of lashes and lash-like terminal hairs.

Alcon, Inc. ("Alcon") introduced a prostaglandin F2a analog, commonly known as Travoprost whose chemical name is isopropyl(z)-7-[(1R,2R,3R,5S)-3,5-dihydroxy-2-[(1E, 3R)-3-hydroxy-4-[(α,α,α-trifluoro-m-tolyl)oxy]-1-butenyl]cyclopentyl]-5-heptenoate as a glaucoma treatment. Alcon also sought patent protection for Travoprost for growing hair in U.S. Patent Application No. 2003/0199590.

Allergan, Inc. ("Allergan") introduced Bimatoprost whose chemical name is cyclopentane N-ethyl haptanamide-5-cis-2-(3α-hydrosy-5-phenyl-1-trans-pentenyl)-3,5-dihydroxy, [1α, 2α, 3α, 5α) for treating glaucoma. U.S. Pat. No. 7,351,404 is directed at the use of this molecule and similar molecules for growing hair, including eyelashes. Allergan distinguishes the Bimatoprost molecule from other prostaglandins on the basis that Bimatoprost is a prostamide.

U.S. Pat. Nos. 5,886,035 and 5,985,920 describe fluorine containing prostaglandin derivatives for use as a preventive or therapeutic medicine for an eye disease such as glaucoma or elevated intraocular pressure.

BRIEF DESCRIPTION OF THE DRAWINGS

FIG. 1 shows a process flow from a Corey acetate derivative to a difluoro compound that includes an ethyl amide.

DETAILED DESCRIPTION

Compositions for topical application, methods of topical application of a composition to enhance hair, and a kit are described. Enhancing hair as used herein includes stimulating or promoting growth of existing hair, including stimulating or promoting a bulb or cells in a follicle associated with the formation of an actual hair into hair growth. Hair growth in this sense includes an increase in length and/or an increase in diameter of a hair. Enhancing hair also includes conditioning hair and/or cosmetically improving the appearance or beauty of the hair such that hair subject to the compound or a composition including the compound appears or feels longer, thicker and fuller. Enhancing hair also includes darkening the hair. The location of the hair includes the scalp (e.g., scalp hair), eyelid (e.g., eyelashes), and brow (e.g., eyebrows) and any other portion of human skin where hair exists or may be desired.

In one embodiment, a composition includes an effective hair enhancing amount of a compound represented by the following formula:

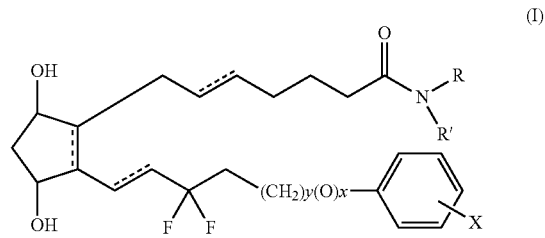

wherein the dashed bonds represent a single or double bond that can be in the cis or trans configuration; R and R' are individually selected from hydrogen, or a $C_1$-$C_6$ straight or branched chain alkyl (e.g., methyl, ethyl, isopropyl); X is a halide (e.g., F, Cl, Br, I) a halide-containing group (e.g., $CF_3$), or hydrogen; either y=0 and x=1 or y=1 and x=0. The molecule may be characterized as a difluoro prostaglandin or prostaglandin-like compound because its backbone resembles a prostaglandin.

A difluoro compound may be in a molecular free form (a molecule) or an acceptable salt thereof (a compound). An acceptable salt is a dermatologically acceptable salt or a pharmaceutically acceptable salt. An example of a salt is a hydrohalide salt of the molecule such as a hydrochloride salt. In one embodiment, the resulting salt compound will have the proton from the hydrohalide bonded to the nitrogen of the molecule and be charge balanced by the halide. Throughout this description, unless specifically indicated a reference to a compound includes a molecule or a compound.

In another embodiment, the compound has the following formula:

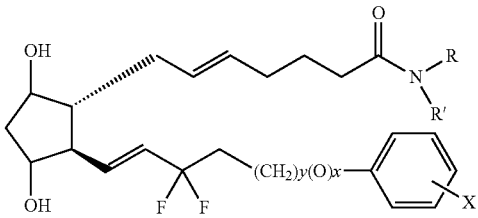
(II)

wherein R, R', X, y and x are defined above, or an acceptable salt thereof.

In a particular embodiment, the compound is one of the following molecules or a salt thereof:

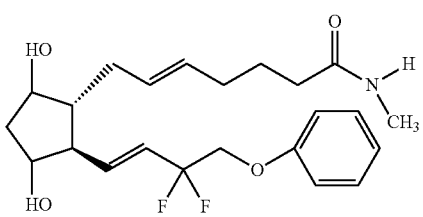
(1)

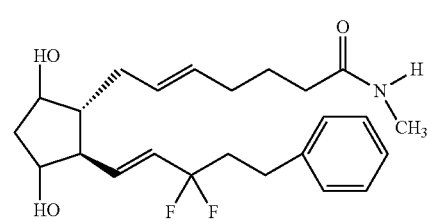
(2)

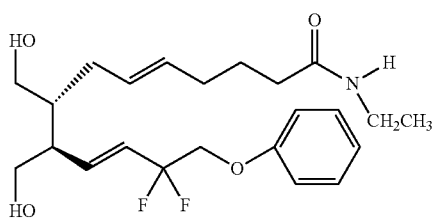
(3)

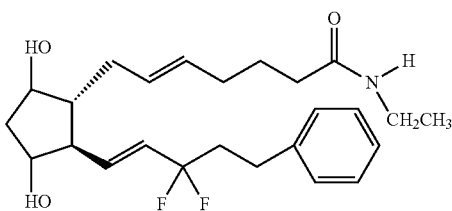
(4)

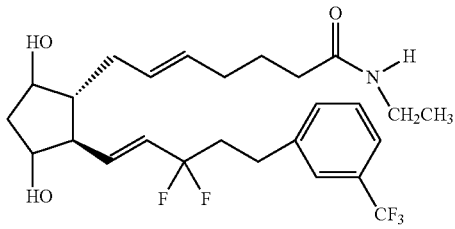
(5)

In one embodiment, one or more compounds described above is/are mixed with a dermatologically compatible vehicle or carrier to form a composition. Suitable vehicles include, for example, aqueous solutions such as e.g., physiological salines, oil (e.g., castor oil), solutions, foams, creams or ointments. Suitable vehicles furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

In one embodiment, dermatological compositions for topical treatment for enhancing hair that include an effective hair enhancing amount of one or more compounds as defined above and a dermatologically compatible carrier are also disclosed. Effective amounts of the active compounds may be determined by one of ordinary skill in the art but will vary depending on the compound employed, frequency of application and desired result. An amount of a compound or compounds will generally range from about 0.0000001 to about 10 percent, by weight, of the dermatological composition, preferably from about 0.0001 to about 10 percent, by weight, of total dermatological composition.

In another embodiment, a composition may include a combination of difluoro prostaglandin or prostaglandin-like compounds described or a compound(s) and other hair treatment aids such as an antioxidant (e.g., Vitamin E), a vasodilator (e.g., minoxidil), an antimicrobial (e.g., benzoyl peroxide), or an anti-inflammatory (e.g., hydrocortisone, cyclooxygenase inhibitor, lipooxigenase inhibitor).

The composition may be topically applied to the dermis of, for example, a human in an area desired for enhancing hair such as direct application to existing hair or the dermis in an area desired for hair enhancing as opposed to an indirect application such as to the surface of the eye. Such location may include the scalp, eyelash area or eyelid or brow of a male or female. Application of the compound(s) or composition to a base of a hair or hairs may create a wicking action where the compound(s) are drawn up the length of the hair or hairs. Repeated application for a sustained period of time (e.g., daily for several weeks or more (e.g., one month to several months)) may be desired.

Where hair is not present, the composition may be applied directly to the dermis where hair growth is desired. This may include the scalp where, for example, a density of existing hair has been reduced due to alopecia or other mechanism (e.g., hair loss as a side effect to chemotherapy treatment). In certain Asian cultures, an absence of pubic hair is considered bad luck and can be a serious problem, particularly in women. The composition may be applied to the pubic area to address this problem. In one embodiment, repeated daily topical application of a composition to an area of the dermis where hair growth is desired may continue until hair growth is effected and may continue periodically (daily, weekly) to maintain such growth. In one embodiment, such topical application to the dermis may, for example, utilize a delivery vehicle including the composition that is a foam or cream.

To enhance eyelashes, a composition including at least one difluoro prostaglandin or prostaglandin-like compound as described above may be applied at the base of an eyelid adjacent to or where hair grows from the follicles (e.g., along the lash line). Alternatively or additionally, the composition may be applied to the eyelashes themselves. Repeated application for consecutive days, weeks or months (e.g., regular daily application for six months) of the composition to eyelashes or areas of eyelid dermis associated with eyelashes (e.g., the base of an eyelid containing follicles in which eyelashes grow) will condition and cosmetically enhance existing eyelashes such that the eyelashes appear longer, thicker and fuller. Such application will also stimulate or promote the growth of eyelashes.

In another embodiment, a kit is disclosed. The kit may include the composition of at least one difluoro prostaglandin or prostaglandin-like compound as described above in a dermatologically compatible vehicle or carrier in a container. The container includes an amount of the composition for repeated application over a period, such as enough of the composition for daily application over a period of six months. The container may also include an applicator, such as a mascara brush or other instrument for application of the composition to skin. In the case of a composition in the form of a foam, the container may be pressurized and include a nozzle to dispense a desired amount onto the hand of a user.

EXAMPLE 1

Synthesis of 3,3-difluoro-4-phenoxybut-1-enyl-3,5-dihydroxycyclopentyl-hept-5-enoic acid Starting from a Corey acetate derivative, an omega chain backbone, such as dimethyl 2-oxo-3-phenoxy-propyl phosphonate is added via an exchange reaction. The oxo group in the 2 position is preserved in the formed intermediate and then reduced with a fluorine compound to produce a difluoro precursor. Subsequently, the alpha chain is added at another site of the Corey acetate derivative yielding 3,3-difluoro-4-phenoxybut-1-enyl-3,5-dihydroxycyclopentyl-hept-5-enoic acid.

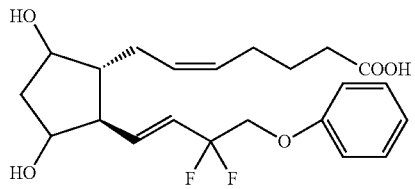 [SMILES: O=C(O)CCC/C=C\C[C@H]1C(O)CC(O)[C@@H]1/C=C/C(F)(F)COc1ccccc1]

EXAMPLE 2

Synthesis of 3,3-difluoro-4-phenoxybut-1-enyl-3,5-dihydroxycyclopentyl-menthylhept-5-enoate To the 3,3-difluoro-4-phenoxybut-1-enyl-3,5-dihydroxycyclopentyl-hept-5-enoic acid is added iodomethane in a solution of tetrahydroturan (THF) to form 3,3-difluoro-4-phenoxybut-1-enyl-3,5-dihydroxycyclopentyl-methylhept-5-enoate.

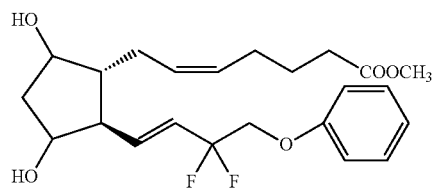 [SMILES: COC(=O)CCC/C=C\C[C@H]1C(O)CC(O)[C@@H]1/C=C/C(F)(F)COc1ccccc1]

EXAMPLE 3

Synthesis of 3,3-difluoro-4-phenoxybut-1-enyl-3,5-dihydroxycyclopentyl-N-ethylhept-5-enamide To the 3,3-difluoro-4-phenoxybut-1-enyl-3,5-dihydroxycyclopentyl-methylhept-5-enoate is added ethylamine in water to form 3,3-difluoro-4-phenoxybut-1-enyl-3,5-dihydroxycyclopentyl-N-ethylhept-5-enamide.

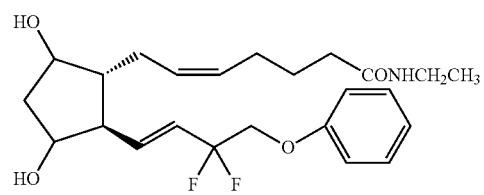

FIG. 1 shows a process flow from a Corey acetate derivative to the acid, to the ester and then to an ethyl amide (Compound 3). U.S. Pat. No. 5,886,035 also describes a method of preparing difluoro-prostaglandin derivatives but does not describe the use of such derivatives in hair (eyelash) growth.

The following examples provide representative compositions including a difluoro compound such as Compound 3:

EXAMPLE 4

Eyelash Composition

| Ingredient | Percentage |
|---|---|
| 1. Water (Aqua) | 97.791 |
| 2. Sodium Chloride | 0.877 |
| 3. Panthenol | 0.020 |
| 4. Citric Acid | 0.030 |
| 5. Phenoxyethanol | 0.300 |
| 6. Chlorphenesin | 0.300 |
| 7. Disodium Phosphate | 0.142 |
| 8. Difluoro Compound | 0.024 |
| 9. Alcohol | 0.216 |
| 10. Cellulose Gum | 0.300 |

EXAMPLE 5

Eyelash Composition

| Ingredient | Percentage |
|---|---|
| 1. USP Water | 94.519 |
| 2. Sodium Chloride | 0.077 |
| 3. Phosphoric Acid | 0.03 |
| 4. Phenoxyethanol | 0.3 |

| Ingredient | Percentage |
| --- | --- |
| 5. Chlorphenesin | 0.3 |
| 6. Disodium Phosphate | 0.142 |
| 7. Cellulose Gum | 0.36 |
| 8. Biotin | 0.5 |
| 9. Glycerin | 0.6 |
| 10. *Swertia Japonica* Extract | 0.045 |
| 11. Saw Palmetto Extract | 0.064 |
| 12. *Camellia Sinensis* (White Tea) Leaf Extract | 0.054 |
| 13. *Panax Ginseng* | 0.075 |
| 14. Octapeptide-2 | 0.93 |
| 15. Biotinoyl Tripeptide-1 | 0.93 |
| 16. Wheat Protein | 0.25 |
| 17. *Calendula* | 0.8 |
| 18. Difluoro Compound | 0.024 |

EXAMPLE 6

Eyelash Composition

| Ingredient | Percentage |
| --- | --- |
| 1. USP Water | 96.031 |
| 2. Actiphyte of Rosemary | 0.025 |
| 3. Phosphoric Acid | 0.001 |
| 4. Phenoxyethanol | 0.3 |
| 5. Chlorphenesin | 0.3 |
| 6. Disodium Phosphate | 0.985 |
| 7. Cellulose Gum | 0.36 |
| 8. Biotin | 0.24 |
| 9. Panthenol | 0.25 |
| 10. Actiphyte of Nettles | 0.1 |
| 11. Actiphyte of Horsetail | 0.098 |
| 12. Actiphyte of *Psoralea* Seed | 0.15 |
| 13. Mulberry Root Extract | 0.07 |
| 14. Actiphyte of Japanese Green Tea | 0.25 |
| 15. Glycerin | 0.6 |
| 16. Difluoro Compound (in 10% Ethanol Solution) | 0.24 |

EXAMPLE 7

Scalp Composition

| Ingredient | Percentage |
| --- | --- |
| 1. Water | 95.00000 |
| 2. Acrylates Copolymer | 1.50000 |
| 3. Glycerin | 1.00000 |
| 4. Phenoxyethanol | 0.80000 |
| 5. Sodium Cocoyl Glutamate | 0.35000 |
| 6. Chlorphenesin | 0.30000 |
| 7. Polysorbate | 0.25000 |
| 8. Trifluoromethyl Dechloro Ethylprostenolamide | 0.24000 |
| 9. Disodium EDTA | 0.10000 |
| 10. Fragrance | 0.09610 |
| 11. Aminomethyl Propanol | 0.09000 |
| 12. *Panax Ginseng* Root Extract | 0.08000 |
| 13. Panthenol | 0.08000 |
| 14. *Ginko Bilola* Leaf Extract | 0.05000 |
| 15. Biotin | 0.05000 |
| 16. *Serenoa Serrulata* Fruit Extract | 0.00640 |
| 17. *Swertia Japonica* Extract | 0.00450 |
| 18. Hydrolyzed Wheat Protein | 0.00300 |

In another embodiment, compositions for topical application and methods of topical application of a composition to modify hair are described wherein the modification includes increased curl of hair on a subject or hair that is not biologically attached to or is not naturally a part of a subject (e.g., hair of a wig or extension) ("non-natural hair"). In another embodiment, the modification includes increased curl of the hair together with conditioning hair and/or cosmetically improving the appearance or beauty of the hair (e.g., increased look and feel of softness and silkiness). Thus, the compositions described may be applied to existing hair on the scalp or eyelashes or non-natural hair to increase the curl and/or the look and feel of the hair. In one embodiment, a composition includes an effective amount of a compound represented by the following formula:

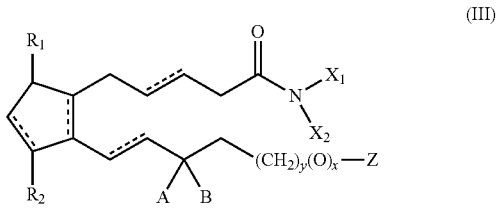

(III)

wherein the dashed bonds represent a single or double bond and when a bond in either chain is a double bond, cis or trans configuration is contemplated;

wherein A and B are individually selected from a hydrogen atom, a hydroxyl group (—OH) and a halogen atom (e.g., a fluorine atom), with the proviso that when one of A and B is a hydroxyl group, the other of A and B is a hydrogen atom and when one of A and B is a halogen atom, the other of A and B is a halogen atom or a hydrogen atom;

wherein Z is a cycloalkyl moiety having from three to seven carbon atoms, an aryl moiety including from four to ten carbon atoms or a heteroaryl moiety including three to nine carbon atoms and at least one heteroatom selected from nitrogen, oxygen and sulfur; and wherein $X_1$ and $X_2$ are individually selected from a hydrogen atom, an alkyl moiety having from one to six carbon atoms,

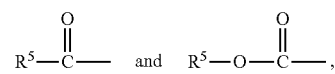

and $R^5$ is an alkyl moiety having from one to six carbon atoms;

wherein $R_1$ and $R_2$ are individually selected from an oxo group (=O), a hydroxyl group (—OH) or an ester group (—O(CO)$R_6$), and $R_6$ is a saturated or unsaturated acyclic hydrocarbon group having from 1 to about 20 carbon atoms, and —(CH$_2$)$_m$R$_7$ wherein m is 0 or an integer of from 1 to 10, and $R_7$ is cycloalkyl group, having from three to seven carbon atoms, or an aryl or heteroaryl group, as defined above;

wherein y is 0 or 1, x is 0 or 1 and x and y are not both 1.

The compound may be in free form (a molecule) or an acceptable salt thereof (a compound) such as a cationic or anionic salt formed at the nitrogen atom of the molecule, in association with a carrier adapted for topical application to mammalian skin. Unless specified, reference to a compound will include a molecule or a compound.

In one embodiment, the compound is represented by the following formula:

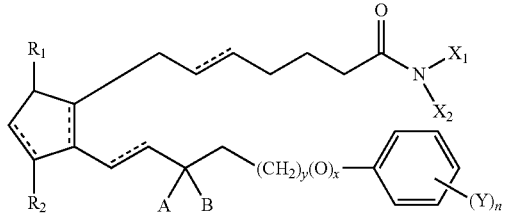
(IV)

wherein Y is selected from an alkyl group, a halogen atom (e.g., fluorine, chlorine), a nitro group, an amino group, a thiol group, a hydroxy group, an alkyloxy group, an alkylcarboxy group, a halo substituted alkyl wherein the alkyl includes from one to six carbon atoms, and n is 0 or an integer of from 1 to 3, or an acceptable salt thereof.

In another embodiment, the compound has the following formula:

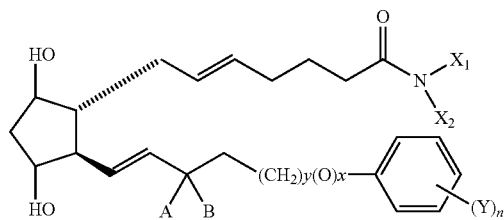

wherein A, B, $X_1$, $X_2$, Y and n are as defined above, or an acceptable salt thereof.

In a particular embodiment, the compound is selected from any of compounds (1)-(5) above or a molecule having one of the following formulas or a salt thereof:

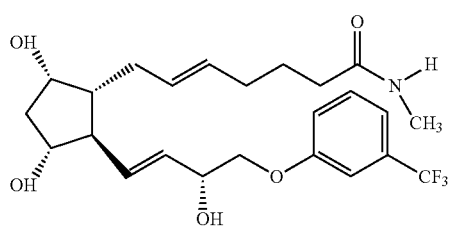
(6)

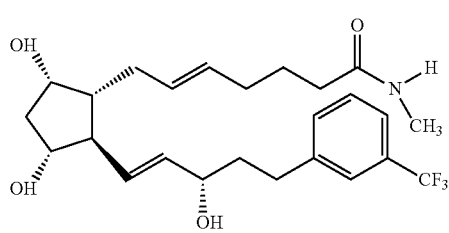
(7)

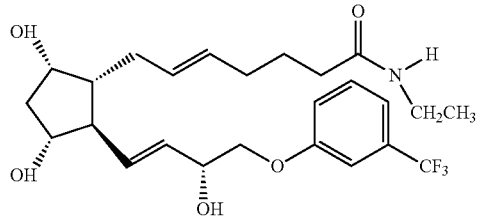
(8)

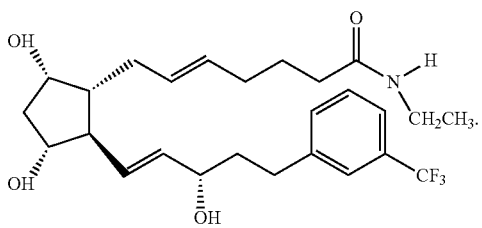
(9)

Compounds (6)-(9) may be prepared using techniques known in the art including, for example, techniques described in U.S. Pat. Nos. 5,001,153; 5,422,368; 5,510,383; and 5,607,978.

In one embodiment, the one or more compounds described above (including compounds (1)-(9) is/are mixed with a dermatologically compatible vehicle or carrier. Suitable vehicles include, for example, aqueous solutions such as e.g., physiological salines, oil (e.g., castor oil), water solutions, water/alcohol solutions or ointments. Suitable vehicles furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

In one embodiment, dermatological compositions for topical treatment for inducing or stimulating modification of existing hair including increased curl which include an effective hair modifying amount of one or more compounds as defined above and a dermatologically compatible carrier are also disclosed wherein the modification includes increased curl of hair or increased curl. Effective amounts of the compound may be determined by one of ordinary skill in the art but will vary depending on the compound employed, frequency of application and desired result, and the compound will generally range from about 0.0000001 to about 50%, by weight, of the dermatological composition, preferably from about 0.001 to about 50%, by weight, of total dermatological composition, more preferably from about 0.1 to about 30%, by weight of the composition. In another embodiment, a composition may include a combination of compounds described or a compound(s) and other hair treatment aids such as an antioxidant (e.g., Vitamin E), a vasodilator (e.g., minoxidil), an antimicrobial (e.g., benzoyl peroxide), or an anti-inflammatory (e.g., hydrocortisone, cyclooxygenase inhibitor, lipooxigenase inhibitor).

The composition may be topically applied to existing hair and retained on the hair. Such location may include the scalp or eyelash area of a male or female. Repeated application for a sustained period of time (e.g., daily for several weeks or more (e.g., one month to several months)) may be desired. The composition may be beneficial to persons that naturally have straight scalp hair to aid in the curl of such hair. Evidence of the effectiveness of a composition of compound (3) (dechloro-dihydroxy-difluoro-ethylcloprostenate) and, alternatively, of compound (8) (trifluoromethyl dechloroethyl prostenolamide) in application to generally straight Asian hair indicates a profound curling effect.

In one embodiment, the composition is suitable for modifying eyelashes. To modify eyelashes, a composition would be provided to a subject with instructions on use (e.g., by instructions on or with a kit, the kit including the composition and the instructions). The subject would be instructed to apply the composition to eyelash hair. In addition to modifying the eyelashes (e.g., increasing the curl and/or look and feel), it is anticipated that application to a hair follicle will increase the thickness (e.g., diameter) of the follicle.

In one embodiment, the composition may be topically applied to hair on the scalp. For example, a subject interested in establishing a curl to a portion of the subject's scalp hair or improving a natural curl, would be instructed (e.g., by instructions on or with a kit) to topically apply the composition to the desired portion of the hair and to leave the composition on the hair. To improve or sustain the curl over a period of time (e.g., days, weeks), the subject would be instructed to repeat the application for a period ranging from days to weeks.

In another embodiment, the applications described above may be used to modify non-natural hair (e.g., hair not biologically attached to or is not naturally a part of a subject). Examples of such hair include, but are not limited to, wigs and hair extensions.

In another embodiment, a kit is disclosed. The kit may include the composition of at least one compound having the formula III or IV as described above in a dermatologically compatible vehicle or carrier in a container. The container includes an amount of the composition for repeated application over a period, such as enough of the composition for daily application over a period of six months. The container may also include an applicator, such as a mascara brush or other instrument for application of the composition to skin. In the case of a composition in the form of a foam, the container may be pressurized and include a nozzle to dispense a desired amount onto the hand of a user.

EXAMPLE

The following example used trifluoromethyl dechloroethyl prostenolamide (TDP) as a compound. TDP has the following formula:

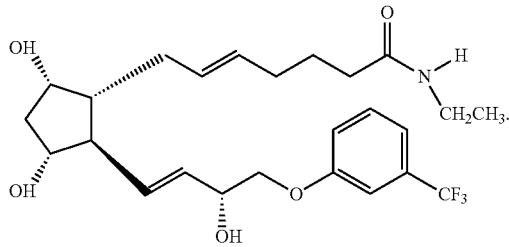 [SMILES: CCNC(=O)CCC/C=C/C[C@@H]1[C@@H](/C=C/[C@@H](O)COc2cccc(C(F)(F)F)c2)[C@H](O)C[C@@H]1O]

A solution of TDP was prepared including 97.6 percent water, 0.24 percent TDP and 2.16 percent ethyl alcohol. Samples of human hair separated from a subject were treated with water alone while others were treated with the TDP solution. The treatment involved dipping the dry hair samples into the water and TDP solutions to one minute. Unexpectedly, there appeared a definite increase in curl in each of the hair samples when treated with the TDP solution. The hair treated with water alone did not show similar curl. The results are illustrated in FIG. 1. In addition, the hair treated with the TDP solution had a noticeable and palpable increase in the look and feel of softness and silkiness compared to the hair treated with the water alone.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
   directly applying to hair an effective hair curling amount of a composition to increase a curl of the hair, the composition comprising a compound of the formula:

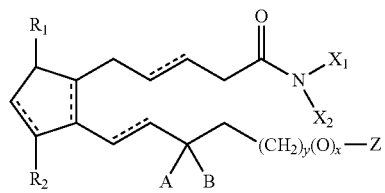

wherein the dashed bonds represent a single or double bond;

wherein A and B are each a fluorine atom;

wherein Z is a cycloalkyl moiety having from three to seven carbon atoms, an aryl moiety including from four to ten carbon atoms or a heteroaryl moiety including three to nine carbon atoms and at least one heteroatom selected from nitrogen, oxygen and sulfur; and wherein $X_1$ and $X_2$ are individually selected from a hydrogen atom, an alkyl moiety having from one to six carbon atoms,

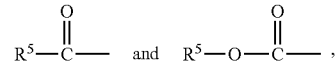

and $R^5$ is an alkyl moiety having from one to six carbon atoms;

wherein $R_1$ and $R_2$ are individually selected from an oxo group, a hydroxyl group or an ester group, and $R_6$ is a saturated or unsaturated acyclic hydrocarbon group having from 1 to about 20 carbon atoms, and $—(CH_2)_m R_7$ wherein m is 0 or an integer of from 1 to 10, and $R_7$ is cycloalkyl group, having from three to seven carbon atoms, or an aryl or heteroaryl group, as defined above;

wherein y is 0 or 1, x is 0 or 1 and x and y are not both 1, or a salt thereof; and leaving the composition on the hair.

2. The method of claim 1, wherein the hair comprises eyelashes.